United States Patent [19]
Nelson

[11] Patent Number: 5,513,657
[45] Date of Patent: May 7, 1996

[54] WRIST BRACE

[76] Inventor: Ronald E. Nelson, 1120 Second St., Box 441, Chetek, Wis. 54728

[21] Appl. No.: 373,010

[22] Filed: Jan. 17, 1995

[51] Int. Cl.$^6$ ................................. A61F 5/37; A61F 5/00
[52] U.S. Cl. ............................... 128/879; 602/20; 602/21
[58] Field of Search .................................. 602/20, 21, 22, 602/5; 2/2, 16; 128/846, 877, 878, 879; 473/61, 62, 60

[56] References Cited

U.S. PATENT DOCUMENTS

| | | |
|---|---|---|
| 2,794,638 | 6/1957 | Risher et al. |
| 3,049,717 | 8/1962 | Meyer ........................................ 2/16 |
| 3,238,939 | 3/1966 | Stubbs. |
| 3,327,703 | 6/1967 | Gamm. |
| 3,512,776 | 5/1970 | Thomas ..................................... 473/62 |
| 3,533,407 | 10/1970 | Smith. |
| 3,598,408 | 8/1971 | Klose. |
| 3,606,319 | 9/1971 | Borden ..................................... 473/61 |
| 3,728,738 | 4/1973 | Andolino ................................. 473/62 |
| 3,815,908 | 6/1974 | Hashimoto ............................... 602/64 |
| 4,183,098 | 1/1980 | Knowles, Jr. |
| 4,309,991 | 1/1982 | DeMarco. |
| 4,366,812 | 1/1983 | Nuzzo. |
| 4,584,993 | 4/1986 | Nelson ..................................... 602/21 |
| 4,883,073 | 11/1989 | Aziz .......................................... 128/878 |
| 5,267,943 | 12/1993 | Dancyger ................................. 602/20 |

OTHER PUBLICATIONS

BodyBelts, WristBelt, Wrist/Hand Support System.

*Primary Examiner*—Michael A. Brown
*Attorney, Agent, or Firm*—Burd Bartz & Gutenkauf

[57] ABSTRACT

A flexible, elastic wrist brace for use by person's requiring wrist support for engaging in rigorous activity. The brace offers generalized support to the wrist as well as lateral support to limit up and down flexure of the wrist, side to side flexure and longitudinal rotation. The brace includes a base comprised of a flat sheet member of elastic material that is formable into a sleeve. A palmar support member is fixed to the base on the palmar side thereof and includes a pocket containing a resilient stay member. Lateral support assemblies include support members located on the ulnar and radial sides of the base when it is worn on a hand and wrist. The support members are Y-shaped having a trunk and branches that diverge from the trunk. On the radial side, the branches diverge to straddle the thumb joint. On the ulnar side, the branches diverge to straddle the region of the hand interior to the joint of the little finger. Stay members are located in the lateral support members and conform to the Y-shape thereof. First and second support straps extend in opposite directions from the palmar side of the base to locations on opposite sides of the base for added support to the brace.

15 Claims, 3 Drawing Sheets

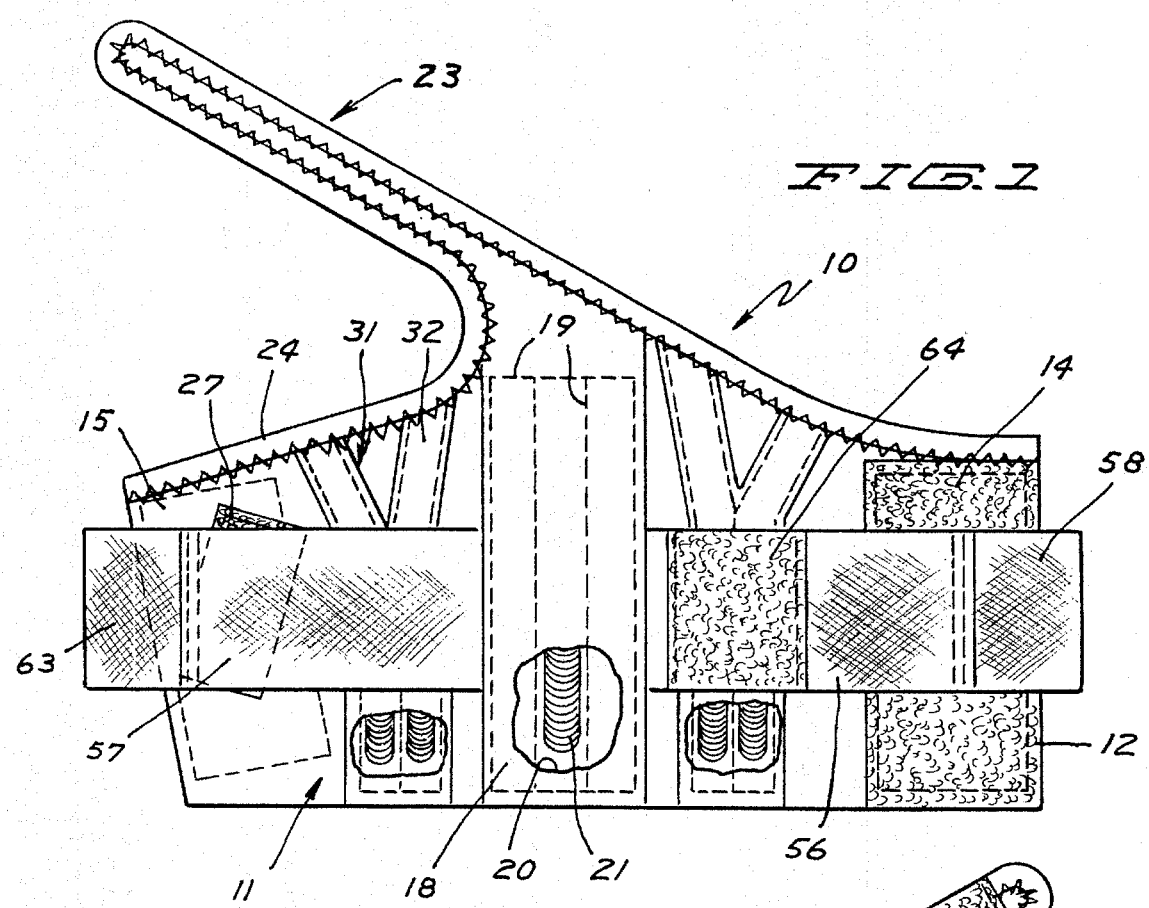
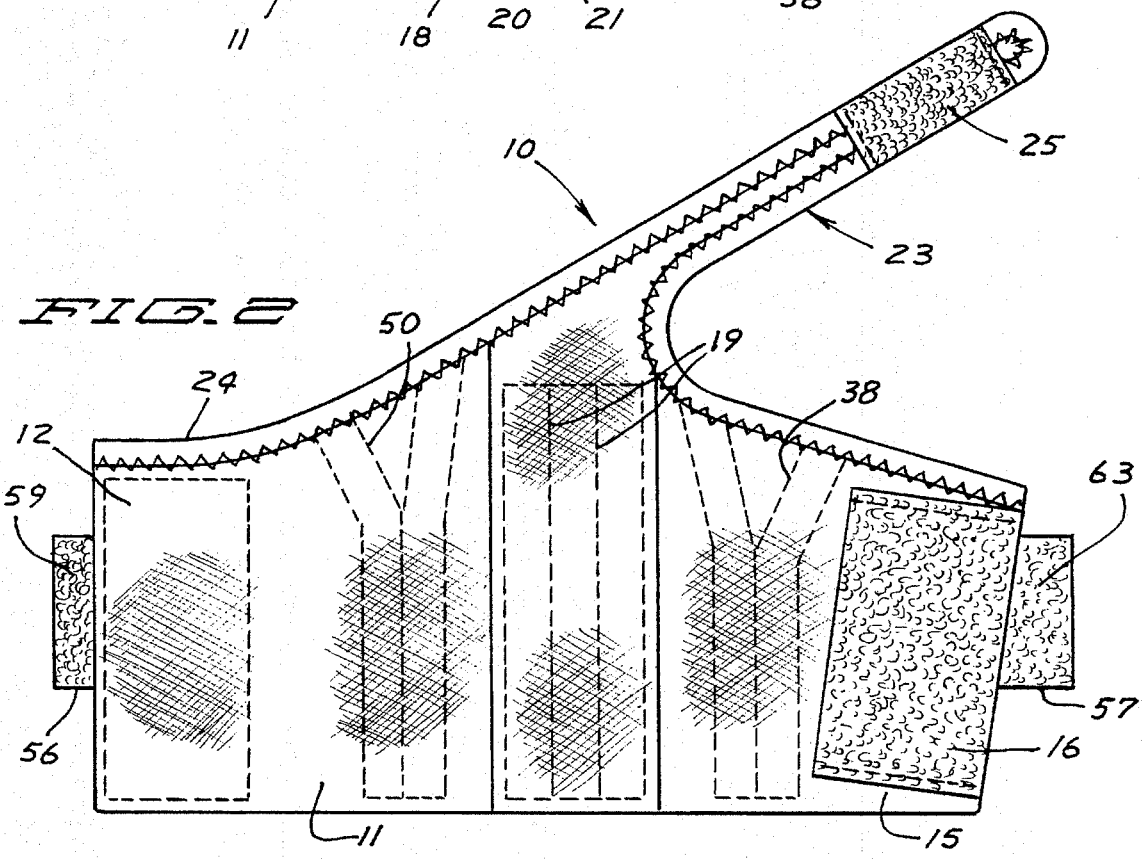

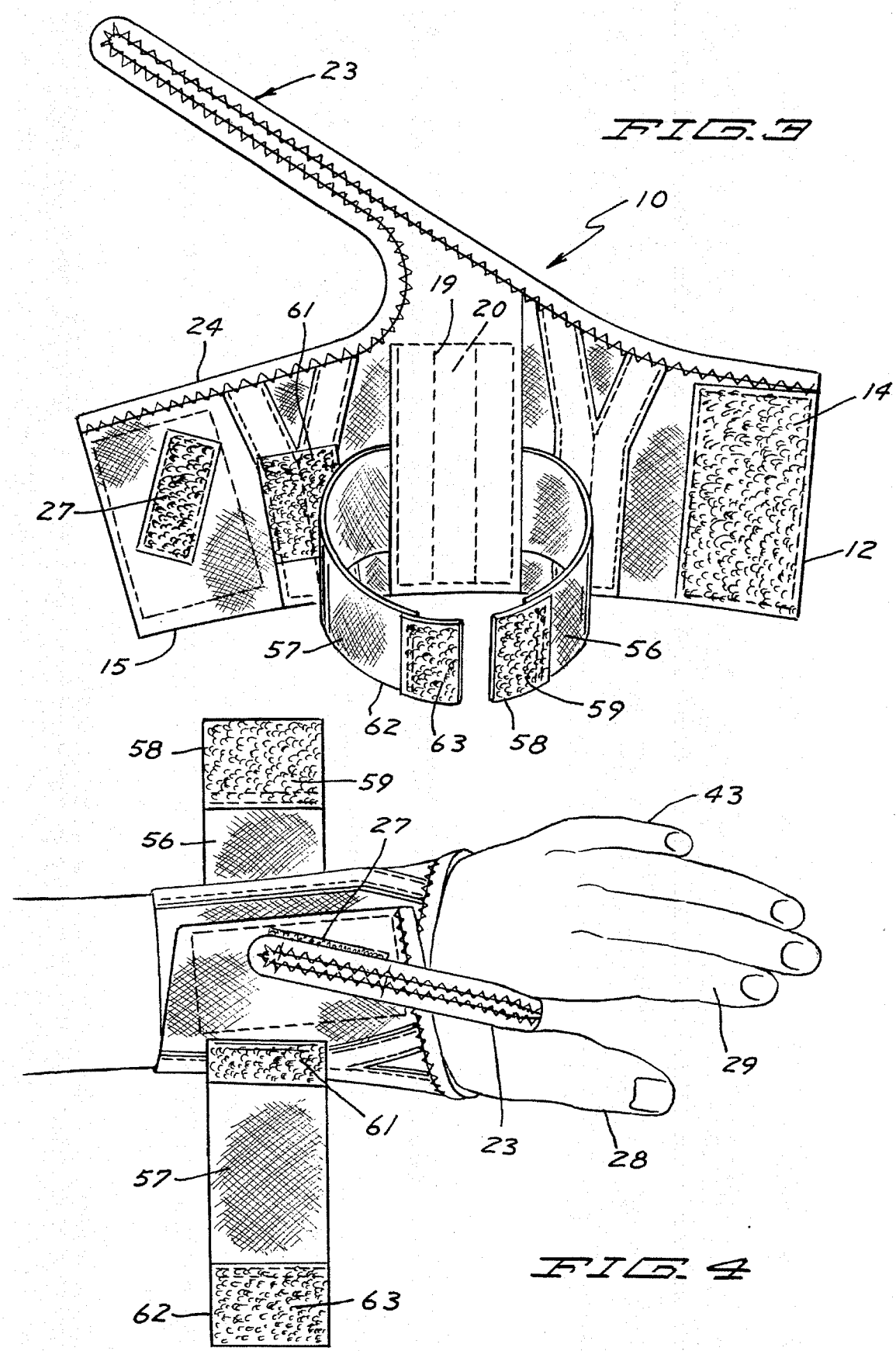

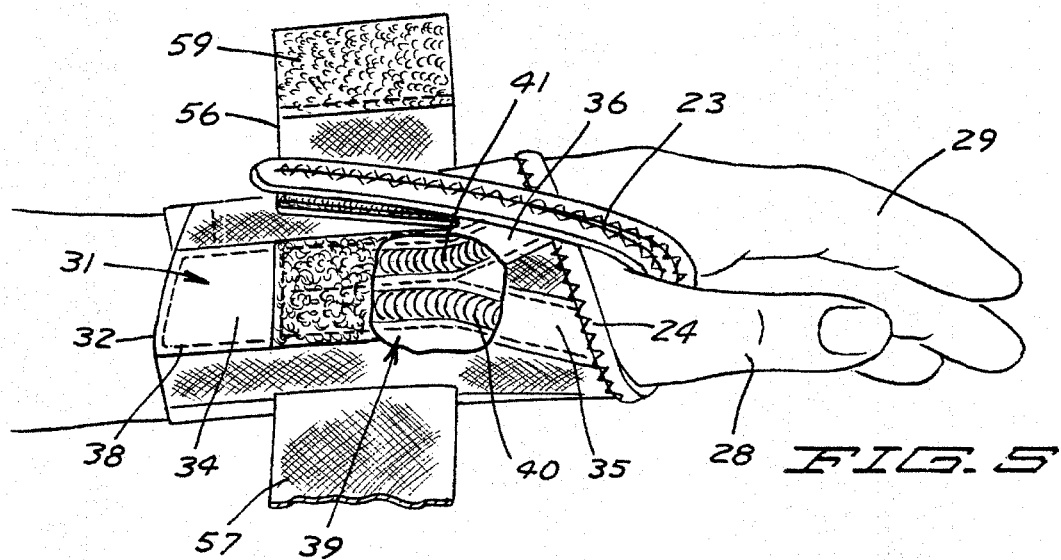
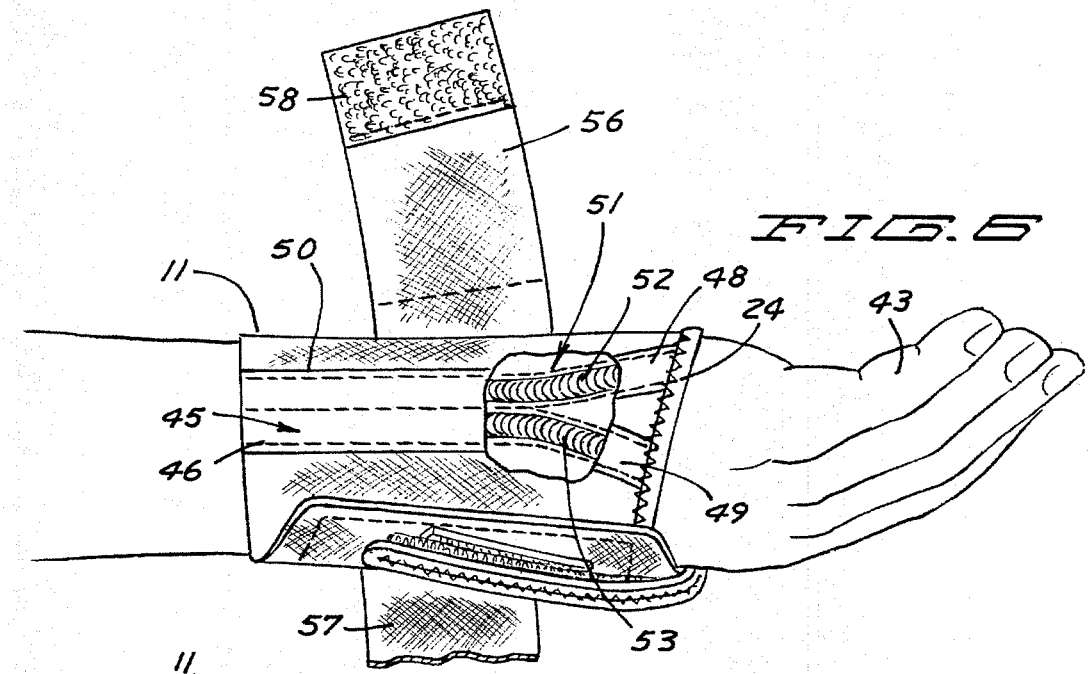
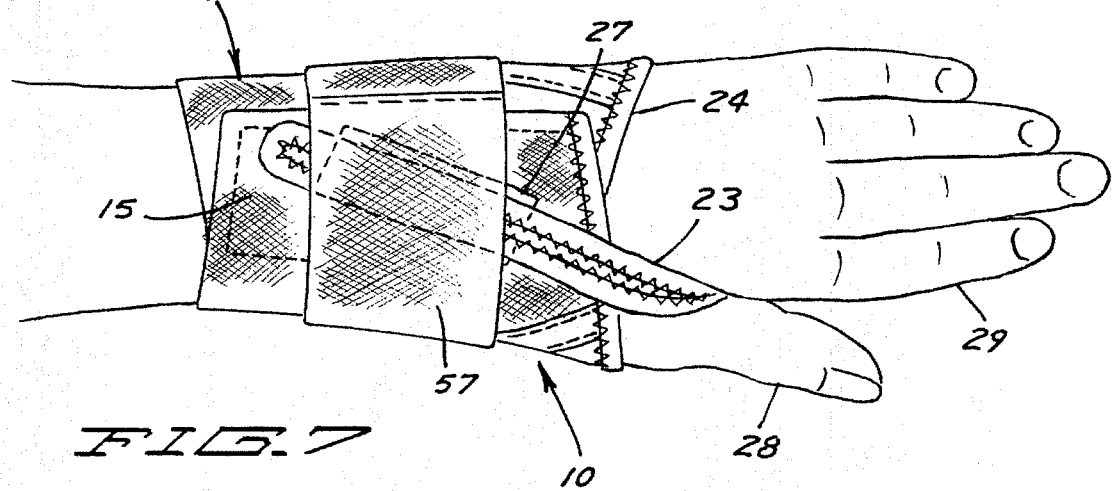

WRIST BRACE

BACKGROUND OF THE INVENTION

The hand and the forearm articulate at the wrist. The two forearm bones are the ulna and the radius. They are joined together by ligaments. The wrist itself is comprised of eight small bones that arranged in two rows of four and are held together by small ligaments. These bones include the carpal bones. The wrist joint is the junction of the two forearm bones and the eight wrist bones. The small size of the bones and ligaments gives a large measure of flexibility and mobility to the wrist joint. The small bones function like universal bearings. The ulna and the radius form a cradle for receipt of these wrist bones.

The ulna is on a lateral side of the wrist or forearm and terminates in the proximity of the hand and little finger. The radius is the larger of the two bones and is on the thumb side. The ulna is substantially stationary and the radius, powered by the forearm muscles, rotates about the ulna rotating the wrist about a longitudinal axis. The wrist is permitted a limited measure of rotation about this longitudinal axis.

Four large tendons are attached to the forearm muscles and move the wrist in four dimensions of freedom: up, down and sideways. Injury to these tendons greatly inhibits the use of the wrist.

In addition, wrist movement is governed by three primary nerves of the arm, which are the radial, ulnar and median nerves.

The various structures of the wrist, the ulna, radius and the eight wrist bones, are interconnected by ligaments. The ligaments are covered by a joint capsule. The tearing of a ligament or a joint capsule is the result of a sprain. This occurs when the wrist is forcibly positioned beyond a normal range of motion, particularly in trauma. When the ligament traumatically extends beyond its normally fixed length, it tends to rip. While most ligament injury occurs when the wrist is being forced downward, injury is also a result of undo twisting of the wrist about a longitudinal axis. A sprain also occurs upon undo movement of the wrist in the side-to-side direction.

It is important, during rigorous activity, to restrain the wrist from motion which will unduly extend the ligaments, in order to prevent a sprain. In addition, once sprained, it is important to protect the wrist against further aggravation. Taping is one popular form of wrist protection. The use of various wrist braces is another.

The same measures in protecting the wrist against sprain are beneficial in protecting the wrist against fracture, although this type of injury is not as common.

SUMMARY OF THE INVENTION

The present invention relates to a flexible wrist brace to be worn by athletes and others engaging in rigorous activity, which requires wrist support or protection in order to protect against wrist injury or protect against aggravation of pre-existent injury. The wrist brace offers generalized support to the wrist area and specifically lateral support to limit flexure of the wrist, support to inhibit undo twisting of the wrist about a longitudinal axis, and support upon a side-to-side movement.

The wrist brace includes a base that is comprised of a flat sheet-like member of elastic material that is stretchable in a circumferential direction to be formed into a sleeve that is positioned around the wrist. The sleeve has a palmar side located on the front or palmar side of the hand; a distal side located opposite, or on the back side of the hand, and ulnar and radial sides located on opposite lateral sides of the hand and wrist. Support members are fixed to the base. A palmar support member is located on the palmar side of the base. This support member includes a pocket enclosing a flexible, resilient stay member. Additional support members are located on the lateral sides of the base. An ulnar support member is located on the side of the base positioned over the ulna; and a radial support member is located on the side of the base positioned over the radius. Each of these support members includes a pocket and a flexible stay member located in the pocket. In a preferred embodiment, each lateral pocket has a wish bone or Y-shape that straddles the side of the hand adjacent the joint of the thumb on the radial side, and the joint of the little finger on the ulnar side of the brace.

First and second elastic support straps have fixed ends on the palmar side of the base on opposite sides of the palmar support member. Free ends are extendible around the base. The straps stretch around the wrist from the palmar side.

An anchor strap is fixed to the base. It is extendable between the thumb and middle finger to the other side of the base in order to fix the position of the base on the wrist and offer a measure of support to the thumb.

IN THE DRAWINGS

FIG. 1 is a side elevation of the outside surface of an unwrapped wrist brace according to the invention with portions fragmented for purposes of illustration;

FIG. 2 is a side elevational view of the inside surface of the unwrapped wrist of FIG. 1;

FIG. 3 is a side elevational view like that of FIG. 1 showing the support straps of the wrist brace in perspective view for purposes of illustration;

FIG. 4 is a side elevational view of a wrist brace according to the invention partially installed on a left hand and viewed from the distal side;

FIG. 5 is a side elevational view of a left hand with a partially-installed wrist brace, viewed from the radial side;

FIG. 6 is a side elevational view from the ulnar side of the hand showing the wrist brace of FIG. 5; and FIG. 7 is a distal view of a wrist brace according to the invention worn on the left hand.

DESCRIPTION OF THE PREFERRED EMBODIMENT

Referring to the drawings, there is shown in FIGS. 1–3 a wrist brace according to the invention, indicated generally at 10. Brace 10 includes a flat base 11 formable into a sleeve to encompass the wrist. Base 11 is left-handed and formed of a linearly elastic fabric preferably stretchable in a single direction, circumferentially around the wrist. Base 11 has lateral edges that wrap around the wrist and come together for fastening when the base in tension and encompassing a wrist.

Base 11 has a first lateral edge 12 that carries an outwardly-facing fastening strip 14. Base 11 has a second lateral edge 15 that carries a second fastening strip 16 that is inwardly facing. The fastening strips 14, 16 are formed of synthetic hook and loop-type material of the type that releasably adheres when pressed together. Base 11 has a generally rectangular shape for wrapping around the wrist in tension. When properly wrapped, the edges 12, 15 meet on the distal side of the wrist. Second fastening strip 16 is overlapped with the first fastening strip 14 and secured thereto to hold the base 11 in place in tension around the wrist.

A palmar support assembly includes a longitudinal, flexible, inelastic support member 18 that is fixed to the base on the palmar side, by suitable means such as peripheral stitching 19 which forms an elongate rectangular pocket 20. An elongate resilient stay member 21 is located in the pocket 20.

An anchor strap 23 extends angularly upward from the outer or upper edge 24 of base 11. The anchor strap 23 is configured specifically to extend from the palmar side of the base 11, between the thumb and index finger (of the left hand for the configuration shown), to a location on the distal side of the hand. The free end of the anchor strap 23 has an inwardly-facing fastening member 25. An outwardly-facing, anchor strap fastening pad 27 (FIG. 3) is located on the outside surface of base 11 on the second lateral edge 15. It is positioned on the distal part of the wrist and outwardly facing when the sleeve is worn on a hand and wrist. The anchor strap 23 extends from the palmar portion of the base, between the thumb 28 and index finger 29, as shown in FIGS. 4, 5 and 7, to a location on the distal side of the wrist. The free end of strap 23 is fastened to the anchor strap fastening pad 27, as best shown in FIG. 4.

Brace 10 has lateral, side support assemblies that contribute generalized support to the wrist, and specifically add support against undo side-to-side rotational movement and longitudinal twisting of the wrist and hand.

A radial support assembly is located on the radial or thumb side of the wrist. The radial support assembly 31 includes an elongated, flexible support member 32. Support member 32 extends between the lower or inward edge of the base 11, and the outer or upper edge 24. It extends from the vicinity of the lower forearm, spanning the wrist joint, terminating in the vicinity of the joint of the thumb. The support member 32 extends along and parallel to a corresponding segment of the radial bone and the aligned wrist segments. The support member 32 is Y-shaped, having a trunk 34 and branches 35, 36. The Y-shaped is outwardly or distally open. Trunk 34 extends from the inward or lower edge of the base 11 to an intermediate position on the wrist. The branches 35, 36 extend angularly away from the trunk 34 and spread from one another to straddle the vicinity of the joint of the thumb. This is shown in FIG. 5.

The radial support member 32 is fixed to the base 11 by stitching 38 that defines an elongate pocket. A Y-shaped stay member 39 is located in the pocket of the support member 32. The Y-shaped stay member 39 is composed of individual stay elements 40, 41, disposed in parallel side-by-side relationship to form a stem located in the trunk 34 of the support member 32. Stay member 39 follows the configuration of the Y-shaped support member 32. The individual stay elements 40, 41 spread apart to extend outwardly from the stem into the branches 35, 36 of the support member 32. The ends of stay elements 40, 41 straddle the vicinity of the joint of the thumb. The stays can be formed of flattened, interleaved helical springs.

A second lateral support assembly is fastened to the base on the ulnar side of the wrist and includes a Y-shaped ulnar support member 45 that is formed of a flexible, inelastic material. Support member 45 extends from the inward edge of the base 11 to the outward edge and spans the vicinity of the wrist on the ulnar side thereof. The ulnar support member 45 is Y-shaped, having a trunk 46 connected to branches 48, 49. The trunk 46 extends from the inward end of the sleeve 11 outwardly toward the hand. Branches 48, 49 extend from the trunk 46 in the vicinity of the joint of the little finger 43.

Stitching 50 defines a pocket between the support member 46 and the base 11. A bifurcated stay member 51 is located in the pocket. Stay member 51 is comprised of individual stay elements 52, 53. The individual stay elements 52, 53 are disposed in side-by-side relationship in the trunk 46 of the support member 45, forming a stem of the stay member 51. The stay elements 52, 53 spread apart beyond the trunk 46 of the support member 45, and are located in the branches 48, 49. The ends of the stay elements straddle the hand near the joint of the little finger. The stay elements 52, 53 are comprised as resilient spring members and, as shown, can be comprised of flattened and interleaved helical springs.

A support strap assembly is provided for securing base 11 to the wrist. A support strap assembly includes a first support strap 56 and a second support strap 57, which extend in opposite directions around the wrist in supportive relationship thereto. Each support strap is comprised of an elastic, linear member fixed at one end to the base 11. The support strap 56 is fixed at one end to the base 11 adjacent the palmar support member 18. It has a free end 58 that is extendable around the wrist when the base 11 is worn on a wrist. The free end 58 of first support strap 56 carries an inwardly-facing support strap fastening pad 59. A corresponding outwardly-facing fastening pad 61 is fastened to the sleeve 11 generally on the radial side thereof. The first support strap 66 is extendable over the ulnar side of the sleeve to the radial side for fastening to the support strap fastening member 61 located on the sleeve. In such arrangement, the strap 56 is placed in tension around the wrist.

The second support strap 57 has a free end 62 which has an inwardly-facing second support strap fastening pad 63. The second support strap 57 is fastened to the base 11 adjacent the palmar support member for extension around the wrist from the palmar side of the base, first around the radial side of the wrist brace, over the distal side and then to the ulnar side. The outward surface of the first support strap 56, near the junction with the palmar support member 18, has an outwardly-facing second support strap fastening member 64. This connects to the second support strap fastening pad 63.

With the first support fastened around the wrist as previously described, the second support strap fastening pad 64 is outwardly facing and is located on the ulnar side of the base. The second support strap 57 is stretched around the radial side of the wrist, the distal side thereof, to an ulnar location poised over the corresponding fastening pad 64 for fastening to it.

In the use of the invention, the wrist brace is initially laid out in the unwrapped configuration shown in FIGS. 1 and 2. The left hand is placed in proper position with respect to the base 11, approaching from the interior side as viewed in FIG. 2. The first lateral edge 12 is wrapped around the arm to the distal side of the wrist. The second lateral edge 15 is wrapped around in the opposite direction with the fastening pad 16 on the second lateral edge engaging the outwardly-facing fastening strip located on the first lateral edge 15. Anchor strap 23 is trained between the thumb and forefinger, extending from the palmar side of the hand to the distal side. The free end 25 engages the anchor strap fastening member 27 located on the distal side of the base 11. When mounted in this configuration, the palmar support assembly, including the palmar support member 18, provides support to the palmar side of the wrist to inhibit downward rotation of the wrist. Lateral support assemblies are in place on the radial and ulnar sides of the wrist. Each includes a Y-shaped support member and having therein a Y-shaped stay member to provide lateral support to the wrist. On the radial side, the Y-shaped support member straddles the base of the thumb. On the ulnar side of the arm, the support member straddles the hand at the base of the little finger.

The support strap assembly firmly pulls the support members into supportive relationship to the hand, wrist and arm. The support straps extend in both directions around the wrist for drawing the base and support members closely in. The first support strap 56 extends from the palmar side of the base, and is stretched around the ulnar side of the base to a location proximate the radial side of the base. The second support strap 57 is stretched from the palmar side of the base in the opposite direction, first around the radial side of the base, over the distal portion of the brace, to the region of the ulnar side of the base. Tensioning the support straps first in one direction around the base and then the other brings the base 11 into a more supportive relationship to the proximate hand, wrist and lower arm. Tension around the base is distributed evenly around the wrist.

While there has been shown and described a preferred embodiment of the invention, it will be apparent that deviations can be had therefrom without departing from the scope and spirit of the invention.

The embodiments of the invention in which an exclusive property or privilege is claimed are defined as follows:

1. A wrist brace comprising:
   a base of sheet material formable into a tubular sleeve having proximal, distal, radial and ulnar sides, closely conformable to corresponding sides of a wrist, and formed of elastic material stretchable in a circumferential direction around a wrist;
   a first lateral support member fastened to the base on the ulnar side, extending generally in parallel and proximate relationship to the ulna in the vicinity of the wrist, said first support member having an elongate, Y-shaped pocket, with the Y-shape distally open and a first resilient stay member located in the pocket;
   a second lateral support member fastened to the base on the radial side, extending generally in parallel and proximate relationship to the radius in the vicinity of the wrist, said second lateral support member having an elongate, Y-shaped pocket with the Y-shape distally open and a second resilient stay member located in the pocket;
   a support strap assembly including first and second support straps, each support strap having a fixed end fixed to the base on the palmar side thereof, said first support strap extendable around the wrist in a first direction and including means for fastening the free end of the first support strap in position around the wrist; and
   said second support strap extendable around the wrist in a second direction, and including means for fastening the free end of the second support strap in position around the wrist.

2. The wrist brace of claim 1 including:
   a palmar support member located on the palmar side of the base and having an elongate pocket, and a palmar stay member located in the pocket.

3. The wrist brace of claim 2 including:
   an anchor strap having one end connected to the base on the palmar side thereof, and a free end extendable between the thumb and index finger to the distal side thereof when the base is installed on a wrist, and means to releasably fasten the free end of the anchor strap on the distal side of the base.

4. The wrist brace of claim 3 wherein:
   said base has first and second lateral edges that come together on the distal side to form said sleeve, and including means for releasably connecting the first and second lateral edges of the base when stretched around a wrist in tension.

5. The wrist brace of claim 4 wherein:
   said means for connecting the lateral edges comprises first and second fastening strips on the first and second lateral edges carrying hook and loop-type fastening means.

6. The wrist brace of claim 4 wherein:
   said anchor strap has a concave edge that generally encompasses the thumb when the free end of the anchor strap is fastened on the distal side of the base.

7. The wrist brace of claim 4 wherein:
   said lateral support members have trunks and branches extended from the trunks;
   said first stay member includes a first stay element and a second stay element disposed in side-by-side relationship in a trunk of the first lateral support member, and extending in diverging relationship in the branches of the first lateral support member;
   said second stay member includes first and second stay elements disposed in side-by-side relationship in the trunk of the second lateral support member, and extending in diverging relationship in the branches of the second support member.

8. A wrist brace comprising:
   a base formable into a tubular sleeve having ulnar, radial, palmar and distal sides to encompass the wrist, with an inward edge located in the vicinity of the lower forearm, and an outward edge located in vicinity of the hand;
   said sleeve formed of a material that is elastically stretchable in a circumferential direction around the wrist;
   a radial support assembly fixed to the base extended from proximate the inward edge of the base to a location at the vicinity of the base of the thumb on the radial side of the wrist, including a resilient radial stay member that is Y-shaped with a stem at the inward end of the base and the bifurcated end toward the outward end of the base; and
   an ulnar support assembly fixed to the base extended from proximate the inward end of the base to a location at the vicinity of the joint of the little finger on the ulnar side of the wrist, including a resilient ulnar stay member that is Y-shaped with a stem end at the inward edge of the base and a bifurcated end at the outward end of the base in straddling relationship to the joint of the little finger.

9. The wrist brace of claim 8 including:
   a support strap assembly having first and second support straps, each support strap having a fixed end fixed to the base on the palmar side thereof, said first support strap extendable around the wrist in a first direction and including means for fastening the free end of the first support strap in position around the wrist; and
   said second support strap extendable around the wrist in a second direction, and including means for fastening the free end of the second support strap in position around the wrist.

10. The wrist brace of claim 9 including:

a radial support member fixed to the radial side of the base and forming a pocket to accommodate the radial resilient stay member; and an ulnar support member fixed to the ulnar side of the base and forming a pocket to accommodate the resilient ulnar stay member.

11. The wrist brace of claim 10 wherein:

said ulnar and radial stay members are each formed of first and second stay elements positioned in parallel relationship at one end to form a stem and spreading apart at the other end to form the Y portion of each stay member.

12. The wrist brace of claim 11 wherein:

said stay elements are formed of flattened, interleaved helical springs.

13. The wrist brace of claim 12 wherein:

said base has first and second lateral edges that come together on the distal side to form said sleeve, and including means for releasably connecting the first and second lateral edges of the base when stretched around a wrist in tension.

14. The wrist brace of claim 13 wherein:

said means for connecting the lateral edges of the base comprises first and second fastening strips on the first and second lateral edges carrying hook and loop-type fastening means.

15. The wrist brace of claim 13 including:

an anchor strap having one end connected to the base on the palmar side thereof, and a free end extendable between the thumb and index finger to the distal side thereof when the base is installed on a wrist, and means to releasably fasten the free end of the anchor strap on the distal side of the base.

\* \* \* \* \*